(12) United States Patent
Vigsnæs et al.

(10) Patent No.: US 11,696,921 B2
(45) Date of Patent: *Jul. 11, 2023

(54) SYNTHETIC COMPOSITION FOR MICROBIOTA MODULATION

(71) Applicant: GLYCOM A/S, Hørsholm (DK)

(72) Inventors: Louise Kristine Vigsnæs, Copenhagen (DK); Bruce McConnell, La Tour de Peilz (CH)

(73) Assignee: GLYCOM A/S, Hørsholm (DK)

( * ) Notice: Subject to any disclaimer, the term of this patent is extended or adjusted under 35 U.S.C. 154(b) by 251 days.

This patent is subject to a terminal disclaimer.

(21) Appl. No.: 17/001,118

(22) Filed: Aug. 24, 2020

(65) Prior Publication Data

US 2021/0000848 A1    Jan. 7, 2021

Related U.S. Application Data

(63) Continuation of application No. 15/759,754, filed as application No. PCT/IB2016/055466 on Sep. 14, 2016, now Pat. No. 10,751,354.

(30) Foreign Application Priority Data

Sep. 14, 2015   (DK) .......................... PA 2015 70589
Feb. 24, 2016   (DK) .......................... PA 2016 70098

(51) Int. Cl.
| | | |
|---|---|---|
| *A61K 31/702* | (2006.01) | |
| *A61P 3/04* | (2006.01) | |
| *A61P 3/10* | (2006.01) | |
| *A61P 1/00* | (2006.01) | |
| *A61K 9/00* | (2006.01) | |

(52) U.S. Cl.
CPC .......... *A61K 31/702* (2013.01); *A61K 9/0053* (2013.01); *A61P 1/00* (2018.01); *A61P 3/04* (2018.01); *A61P 3/10* (2018.01)

(58) Field of Classification Search
None
See application file for complete search history.

(56) References Cited

U.S. PATENT DOCUMENTS

| | | | |
|---|---|---|---|
| 4,782,045 A | 11/1988 | Machida et al. | |
| 9,283,240 B2* | 3/2016 | Buck | A61P 31/14 |
| 9,763,970 B2* | 9/2017 | Buck | A23L 33/125 |
| 2012/0171166 A1* | 7/2012 | Chow | A61K 31/702 |
| | | | 424/93.4 |
| 2014/0037785 A1 | 2/2014 | Barboza et al. | |
| 2014/0335065 A1* | 11/2014 | Davis | A23L 33/40 |
| | | | 424/93.4 |
| 2015/0010670 A1 | 1/2015 | Mills | |
| 2015/0087616 A1 | 3/2015 | Ritter et al. | |

FOREIGN PATENT DOCUMENTS

| | | |
|---|---|---|
| WO | 0104341 A1 | 1/2001 |
| WO | 2007101862 A1 | 9/2007 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012007588 A9 | 1/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013057061 A1 | 4/2013 |

(Continued)

OTHER PUBLICATIONS

Belenguer, A. et al., "Two Routes of Metabolic Cross-Feeding between Bifidobacterium adolescentis and Butyrate-Producing Anaerobes from the Human Gut," Applied and Environmental Microbiology, 2006, vol. 72(5), pp. 3593-3599.

Bezirtzoglou, E. et al., "Microbiota profile in feces of breast- and formula-fed newborns by using fluorescence in situ hybridization (FISH)," Anaerobe, 2011, vol. 17, pp. 478-482.

Blottiere, H.M. et al., "Molecular analysis of the effect of short-chain fatty acids on intestinal cell proliferation," Proceedings of the Nutrition Society, 2003, vol. 62, pp. 101-106.

Bode, L. (2013) "Human milk oligosaccharides and their beneficial effects", Handbook of dietary and nutritional aspects of human breast milk Human Health Handbooks No. 5. (pp. 515-531) The Netherlands: Wageningen Academic Publishers.

(Continued)

*Primary Examiner* — Dale R Miller
(74) *Attorney, Agent, or Firm* — Neal, Gerber & Eisenberg LLP

(57) ABSTRACT

A human milk oligosaccharide (HMO) or a synthetic composition comprising said HMO, for use in increasing the abundance, particularly the relative abundance, of a *Bifidobacterium* of the *B. adolescentis* phylogenic group in the microbiota in the gastro-intestinal tract of a human, preferably a non-infant human. The HMO(s) and/or synthetic composition is useful in; increasing particularly the relative abundance of *B. adolescentis* and/or *B. pseudocatenulatum*; for treating or preventing in said non-infant human with type 2 diabetes and/or obesity; an enteropathogenic infection; impaired gut barrier function and/or; an inflammation related to gastro-intestinal condition, preferably irritable bowel disease (IBD) or irritable bowel syndrome (IBS); as a nutritional composition. The HMO is a fucosylated neutral HMO, a non-fucosylated neutral HMO, or a mixture of a fucosylated and a non-fucosylated neutral HMO. The HMOs comprises 2'-fucosyllactose (preferred), 2'-fucosyllactose (preferred), 3-fucosyllactose, difucosyllactose (preferred), lacto-N-fucopentaose, fucosyl-lacto-N-hexaose, fucosyl-para-lacto-N-hexaose, lacto-N-tetraose (preferred), lacto-N-neotetraose (preferred), lacto-N-hexaose, lacto-N-neohexaose, para-lacto-N-hexaose and para-lacto-N-neohexaose.

16 Claims, No Drawings

(56) References Cited

FOREIGN PATENT DOCUMENTS

| | | |
|---|---|---|
| WO | 2013091660 A1 | 6/2013 |
| WO | 2013139344 A1 | 9/2013 |
| WO | 2014100696 A1 | 6/2014 |
| WO | 2016066175 A1 | 5/2016 |

OTHER PUBLICATIONS

Bottacini, F. et al., "Diversity, ecology and intestinal function of bifidobacteria," Microbial Cell Factories, 2014, vol. 13, pp. 1-15.

Brand-Miller, J.C. et al., "Human milk oligosaccharides are not digested and absorbed in the small intestine of young infants," Proceedings of the Nutrition Society of Australia, 1995, vol. 19, pp. 44.

Buie, T., "Potential Etiologic Factors of Microbiome Disruption in Autism," Clinical Therapeutics, 2015, vol. 37(5), pp. 976-983.

Cani, P.D. et al., "Involvement of gut microbiota in the development of low-grade inflammation and type 2 diabetes associated with obesity," Gut Microbes, 2012, vol. 3(4), pp. 279-288.

Cano, P.G. et al., "Bifidobacterium CECT 7765 Improves Metabolic and Immunological Alterations Associated with Obesity in High-Fat Diet-Fed Mice," Obesity, 2013, vol. 21(11),pp. 2310-2321.

Carey, C.M. et al., "Lactic acid bacteria and bifidobacteria attenuate the proinflammatory response in intestinal epithelial cells induced by *Salmonella enterica* serovar Typhimurium," Can J. Microbiol., 2013, vol. 59, pp. 9-17.

Casen, C. et al., "Deviations in human gut microbiota: a novel diagnostic test for determining dysbiosis in patients with IBS or IBD," Alimentary Pharmacology and Therapeutics, 2015, vo. 42(1), pp. 1-13.

Cha, M.K. et al., "Antiviral activity of Bifidobacterium adolescentis SPM1005-A on human papillomavirus type 16," BMC Medicine, 2012, vol. 10(72), pp. 1-6.

Chen, J. et al., "Bifidobacterium adolescentis supplementation ameliorates visceral fat accumulation and insulin sensitivity in an experimental model of the metabolic syndrome," British Journal of Nutrition, 2012, vol. 107, pp. 1429-1434.

Chen, L.L. et al., "Therapeutic effects of four strains of probiotics on experimental colitis in mice," World J Gastroenterol, 2009, vol. 15(3), pp. 321-327.

Chen, X., "Human Milk Oligosaccharides (HMOS): Structure, Function, and Enzyme-Catalyzed Synthesis," Advances in Carbohydrate Chemistry and Biochemistry, 2015, vol. 72, pp. 113-190.

Chichlowski, M. et al., "Bifidobacteria isolated from infants and cultured on human milk oligosaccharides affect intestinal epithelial function," J Pediatr Gastroenterol Nutr., 2012, vol. 55(3), pp. 321-327.

Duncan, SH et al., "Human colonic microbiota associated with diet, obesity and weight loss," International Journal of Obesity, 2008, vol. 32, pp. 1720-1724.

Duranti, S. et al., "Genomic Characterization and Transcriptional Studies of the Starch-Utilizing Strain Bifidobacterium adolescentis 22L," Applied and Environmental Microbiology, 2014, vol. 80(19), pp. 6080-6090.

Engfer, M.B. et al., "Human milk oligosaccharides are resistant to enzymatic hydrolysis in the upper gastrointestinal tract1-3," The American Journal of Clinical Nutrition, 2000, vol. 71, pp. 1589-1596.

Frick, J.S. et al., "Identification of Commensal Bacterial Strains That Modulate Yersinia enterocolitica and Dextran Sodium Sulfate-Induced Inflammatory Responses: Implications for the Development of Probiotics," Infection and Immunity, 2007, vol. 75(7), pp. 3490-3497.

Fukuda, S. et al., "Bifidobacteria can protect from enteropathogenic infection through production of acetate," Nature, 2011, vol. 469, pp. 543-547.

Fung, I. et al., "Do Bugs Control Our Fate? The Influence of the Microbiome on Autoimmunity," Curr Allergy Asthma Rep, 2012, vol. 12, pp. 511-519.

Gabrielli, O. et al., "Preterm Milk Oligosaccharides During the First Month of Lactation," Pediatrics, 2011, vol. 128 (6), pp. e1520-e1531.

Gill, S.R. et al., "Metagenomic Analysis of the Human Distal Gut Microbiome," Science, 2006, vol. 312(5778), pp. 1355-1359.

Gnoth, M.J. et al., "Human Milk Oligosaccharides are Minimally Digested In Vitro," Journal of Nutrition, 2000, vol. 130(12), pp. 3014-3020.

Guyonnet, D. et al., "Effect of a fermented milk containing Bifidobacterium animalis DN-173 010 on the health-related quality of life and symptoms in irritable bowel syndrome in adults in primary care: a multicentre, randomized, double-blind, controlled trial," Alimentary Pharmacology & Therapeutics, 2007, vol. 26, pp. 475-486.

Hoarau, C. et al., "Supernatant of Bifidobacterium breve induces dendritic cell maturation, activation, and survival through a Toll-like receptor 2 pathway," American Academy of Allergy, Asthma and Immunology, 2006, vol. 117(3), pp. 696-702.

Joossens, M. et al., "Dysbiosis of the faecal microbiota in patients with Crohn's disease and their unaffected relatives," Gut, 2011, vol. 60, pp. 631-637.

Jung, T. et al., "Butyrate modulates bacterial adherence on LS174T human colorectal cells by stimulating mucin secretion and MAPK signaling pathway," Nutritional Research and Practice, 2015, vol. 9(4), pp. 343-349.

Kerckhoffs, A.P.M. et al., "Lower Bifidobacteria counts in both duodenal mucosa-associated and fecal microbiota in irritable bowel syndrome patients," World J Gastroenterol, 2009, vol. 15(23), pp. 2887-2892.

Kim, M.J. et al., "Antiviral activity of Bifidobacterium adolescentis SPM1605 against Coxsackievirus B3," Biotechnology & Biotechnological Equipment, 2014, vol. 28(4), pp. 681-688.

Klindworth, A. et al., "Evaluation of general 16S ribosomal RNA gene PCR primers for classical and next-generation sequencing-based diversity studies," Nucleic Acids Research, 2013, vol. 41(1), pp. 1-11.

Larsen, N. et al., "Gut Microbiota in Human Adults with Type 2 Diabetes Differs from Non-Diabetic Adults," PLoS One, 2010, vol. 5(2), pp. 1-10.

Le, K. et al., "Alterations in fecal Lactobacillus and Bifidobacterium species in type 2 diabetic patients in Southern China population," Frontiers in Physiology, 2013, vol. 3, pp. 1-6.

Ley, R.E. et al., "Microbial ecology: Human gut microbes associated with obesity," Nature, 2006, vol. 444, pp. 1022-1023.

Milani, C. et al., "Evaluation of bifidobacterial community composition in the human gut by means of a targeted amplicon sequencing (ITS) protocol," FEMS Microbiology Ecology, 2014, vol. 90, pp. 493-503.

Mylonaki, M. et al., "Molecular Characterization of Rectal Mucosa-associated Bacterial Flora in Inflammatory Bowel Disease," Inflamm Bowel Dis, 2005, vol. 11(5), pp. 481-487.

Peran, L. et al., "A comparative study of the preventative effects exerted by three probiotics, Bifidobacterium lactis, Lactobacillus casei and Lactobacillus acidophilus, in the TNBS model of rat colitis," Journal of Applied Microbiology, 2007, vol. 103, pp. 836-844.

Pozo-Rubio, T. et al., "Immunostimulatory effect of faecal Bifidobacterium species of breast-fed and formula-fed infants in a peripheral blood mononuclear cell/Caco-2 co-culture system," British Journal of Nutrition, 2011, vol. 106, 1216-1223.

Qin, J. et al., "A human gut microbial gene catalogue established by metagenomic sequencing," Nature, 2010, vol. 454, pp. 59-65.

Schwiertz, A. et al., "Microbiota and SCFA in Lean and Overweight Healthy Subjects," Obesity, 2010, vol. 18(1), pp. 190-195.

Sela, D.A. et al., "Nursing our microbiota: molecular linkages between bifidobacteria and milk oligosaccharides," Trends in Microbiology, 2010, vol. 18(7), pp. 298-307.

Shimotoyodome, A. et al., "Short chain fatty acids but not lactate or succinate stimulate mucus release in the rat colon," Comparative Biochemistry and Physiology, Part A, 2000, vol. 125, pp. 525-531.

Sokol, H. et al., "Low Counts of Faecalibacterium prausnitzii in Colitis Microbiota," Inflamm Bowel Dis, 2009, vol. 15 (8), pp. 1183-1189.

(56) References Cited

OTHER PUBLICATIONS

Talley, N.J. et al., "Irritable bowel syndrome: a little understood organic bowel disease?" The Lancet, 2002, vol. 360, pp. 555-564.

Tojo, R. et al., "Intestinal microbiota in health and disease: Role of bifidobacteria in gut homeostasis," World J Gastroenterol, 2014, vol. 20(41), pp. 15163-15176.

Urashima, T. et al. (2011) Nutrition and Diet Research Progress: Milk Oligosaccharides. New York: Nova Science Publishers, Inc.

Whorwell, P.J., et al., "Efficacy of an Encapsulated Probiotic Bifidobacterium in/antis 35624 in Women with Irritable Bowel Syndrome," American Journal of Gastroenterology, 2006, vol. 101(7), pp. 1581-1590.

Wittmann, A. et al., "Plasmacytoid Dendritic Cells are Crucial in Bifidobacterium adolescentis-Mediated Inhibition of Yersinia enterocolitica Infection," PLoS One, 2013, vol. 8(8), pp. 1-10.

Wu, J. et al., "Bifidobacterium adolescentis supplementation ameliorates visceral fat accumulation and insulin sensitivity in an experimental model of the metabolic syndrome," Dig Dis Sci, 2010, vol. 55, pp. 2814-2820.

Martin, R., et al., "Isolation of Bifidobacteria from Breast Milk and Assessment of the Bifidobacterial Population by PCR-Denaturing Gradient Gel Electrophoresis and Quantitative Real-Time PGR," Applied and Environmental Microbiology, 2009, vol. 75(4), pp. 965-969.

Zivkovic, A.M., et al., "Human milk glycobiome and its impact on the infant gastrointestinal microbiota," PNAS, 2011, vol. 108, pp. 4653-4658.

Bode, L., "Human milk oligosaccharides: Every baby needs a sugar mama," Glycobiology, 2012, vol. 22(9), pp. 1147-1162.

Coppa, G. V., et al., "Oligosaccharides in 4 different milk groups, Bifidobacteria, and Ruminococcus obeum," Journal ol pediatric gastroenterology and nutrition, 2011, vol. 53(1), pp. 80-87.

Wacklin, P., et al., "Secretor genotype (FUT2 gene) is strongly associated with the composition of Bifidobacteria in the human intestine," PloS one, 2011, vol. 6(5), e20113.

"Prevention" in Glossary of medical education terms: Parts 1-7. Wojtczak, A., Ed. Medical Teacher. vol. 24, Nos. 2-6 and vol. 25, No. 1 &2. 2002. (Year: 2002).

* cited by examiner

SYNTHETIC COMPOSITION FOR MICROBIOTA MODULATION

CROSS-REFERENCE TO RELATED APPLICATION

This application is a continuation of U.S. patent application Ser. No. 15/759,754, filed Mar. 13, 2018, now U.S. Pat. No. 10,751,354, which is national stage entry pursuant to 35 U.S.C. § 371 of International Patent Application No. PCT/IB2016/055466, filed on Sep. 14, 2016, which claims priority to Denmark Patent Application No. PA 2015 70589, filed Sep. 14, 2015, and Denmark Patent Application No. PA 2016 70098, filed Feb. 24, 2016, the contents of all of which are fully incorporated herein by reference.

FIELD OF THE INVENTION

This invention relates to a method and composition for modulating the microbiota in the gastro-intestinal tracts of non-infant humans, particularly for increasing the abundance of *Bifidobacterium adolescentis* (*B. adolescentis*) and/or *Bifidobacterium pseudocatenulatum* (*B. pseudocatenulatum*) in the microbiota of non-infant humans. An increased abundance of *B. adolescentis* and/or *B. pseudocatenulatum* in the microbiota of non-infant humans can help to create a more benign intestinal microbial community, which can protect the human host against pathogenic infections and can prevent, or improve resistance to, intestinal and/or extra-intestinal diseases in the host.

BACKGROUND OF THE INVENTION

It has been estimated that the human intestine harbours $10^{13}$ to $10^{14}$ bacterial cells and the number of bacteria outnumbers the total number of cells in the body by a factor of 10 (Gill et al. *Science* 312, 1355 (2006)). The microbiota of the human intestine is a complex and very dynamic microbial ecosystem, which is considered to serve numerous important functions for its human host, including protection against pathogens, induction of immune regulatory functions, nutrient processing and metabolic functions (Tojo *World J. Gastroenterol.* 20, 15163 (2014)). The intestinal microbiota consists of various populations, which are important to preserve human health, and recent research has been able to link imbalances in the intestinal bacterial population to both intestinal and extra-intestinal inflammatory diseases (Buie *Clin. Ther.* 37, 976 (2015); Fung et al. *Curr. Allergy Asthma Rep.* 12, 511 (2012); Ley et al. *Nature* 444, 1022 (2006); Larsen et al. *PLoS One* 5, e9085 (2010)).

Bifidobacteria are considered one of the most beneficial probiotics, and strains of *B. adolescentis* have been widely studied for their effects against specific pathogens. The mechanisms behind the protecting effect include enhancement of the host's immune system and suppression of pathogenic gene expression. A study has recently shown that *B. adolescentis* can protect mice from infection by *Yersinia enterocolitica* by modulating the host intestinal immune system by increasing plasmacytoid dendritic cell and regulatory T-cell frequencies (Wittmann et al *PLoS One* 8, e71338 (2013)). In line with this, an in vitro study has shown that *B. adolescentis* can attenuate pathogen-triggered inflammation by inhibiting IL-8 cell secretion induced by *Salmonella Typhimurium* DT104 (Carey et al. *Can. J. Microbiol.* 59, 9 (2013)). *B. adolescentis* has also been found to have antiviral activity through suppression of viral gene expression (Cha et al. *BMC Med.* 10:72 (2012); Kim et al. *Biotechnol. Biotechnol. Equip.* 28, 681 (2014)). Metabolic end products such as short chain fatty acids (acetate, propionate and butyrate), produced during carbohydrate fermentation, also contribute to intestinal functionality and probiotic attributes of bifidobacteria. It has previously been shown that acetate produced by bifidobacteria can enhance intestinal defence mediated by epithelial cells and thereby protect the host against assault (Fukuda et al. *Nature* 469, 543 (2011)). In addition, while bifidobacteria do not produce butyrate as an end product of fermentation, the importance of metabolic cross-feeding on acetate by butyrate-producing bacteria in the gut has been demonstrated (Belenguer et al *Appl. Environ. Microbiol.* 72, 3593 (2006); Duncan et al. *Int. J. Obes.* 32, 1720 (2008)). Butyrate is the primary energy source for colonocytes and has been reported to regulate the physical and functional integrity of the normal colonic mucosa by altering mucin gene expression (Shimotoyodome et al. *Comp. Biochem. Physiol. A, Mol. Integr. Physiol.* 125, 525 (2000); Blottiére et al. *Proc. Nutr. Soc.* 62, 101 (2003). The increase of mucin protein induced by butyrate, has recently shown to elevate adherence of *B. adolescentis*, which subsequently reduced the adherent ability of *E. coli* (Jung et al. *Nutr. Res. Pract.* 9, 343 (2015)).

Obesity, the major risk factor for type 2 diabetes, is associated with changes in gut microbiota composition. An altered gut microbiota has the potential to affect host metabolism and energy storage and to affect gut permeability, and as a consequence, increase plasma lipopolysaccharides (LPS) and give rise to metabolic endotoxemia and insulin resistance (Cani et al. *Gut Microbes* 3, 279 (2012)). Lower levels of bifidobacteria have previously been detected in obese versus lean and diabetic versus non-diabetic individuals (Duncan et al. *Int. J. Obes.* 32, 1720 (2008); Schwiertz et al. *Obesity* 18, 190 (2010)). *B. adolescentis* in particular has been observed to be underrepresented in type 2 diabetic patients compared to controls (Le et al. *Front. Physiol.* 1 (2013)). Studies have shown that *B. adolescentis* can reduce intestinal permeability (Wu et al. *Dig. Dis. Sci.* 55, 2814 (2010)), and can ameliorate visceral fat accumulation and insulin sensitivity (Chen et al. *Br. J. Nutr.* 107, 1429 (2012)), hence inhibiting the pathological conditions of obesity. Further, *B. pseudocatenulatum*, a member of the *B. adolescentis* phylogenetic group, has been shown to ameliorate both metabolic and immunological dysfunctions related to obesity in a mouse model for obesity (Cano et al. *Obesity.* 21, 2310 (2013)).

The microbial composition has also been suggested to play a role in the pathophysiology of intestinal diseases such as inflammatory bowel disease (IBD) and irritable bowel syndrome (IBS) (Qin et al. *Nature* 464, 59 (2010); Talley et al. *Lancet* 360, 555 (2002)). Alterations in intestinal microbial composition in both IBD and IBS patients have been reported, and studies have revealed a lower number of bifidobacteria in both IBS and IBD compared to healthy subject (Sokol et al. *Inflamm. Bowel Dis.* 15, 1183 (2009); Mylonaki et al. *Inflamm. Bowel Dis.* 11, 481 (2005); Kerckhoffs et al. *World J. Gastroenterol.* 15, 2887 (2009); Casén et al. *Aliment. Pharmacol. Ther.* 42, 71 (2015)). Dysbiosis has recently been established in IBD by characterization of five species including decreased abundance of *B. adolescentis* (Joossens et al. *Gut* 60, 631 (2011)). Certain *Bifidobacterium* species, including *B. adolescentis*, have been reported to provide benefits against conditions like IBD and IBS (Whorwell et al. *Am. J. Gastroenterol.* 101, 1581 (2006); Guyonnet et al. *Aliment. Pharmacol. Ther.* 26, 475 (2007); Chen et al. *World J. Gastroenterol.* 15, 321 (2009); Frick et al. *Infect. Immun.* 75, 3490 (2007)); one mode of action could be the immunomodulatory capacity of these species, acting as IL-10 inducer enhancing an anti-inflammatory immune response (Pozo-Rubio et al. *Br. J. Nutr.* 106, 1216 (2011); Hoarau et al. *J. Allergy Clin. Immunol.* 117, 696 (2006)).

Selective stimulation of specific intestinal bacteria to promote their growth and metabolic activity could be a helpful approach in creating a benign intestinal microbial community. Because some bacteria are able to produce a large selection of carbohydrate active enzymes (such as glycoside-hydrolases and transporters), the bacteria can grow on carbon sources, which may be less easily used by other members of the intestinal microbial community.

Human milk oligosaccharides (HMOs) are a heterogeneous mixture of soluble glycans found in human milk. They are the third most abundant solid component after lactose and lipids in human milk and are present in concentrations of 5-25 g/l (Bode: Human milk oligosaccharides and their beneficial effects. In: *Handbook of dietary and nutritional aspects of human breast milk* (Zibadi et al. (eds.)) pp. 515-32, Wageningen Academic Publishers (2013); Gabrielli et al. *Pediatrics* 128, e1520 (2011)). HMOs are resistant to enzymatic hydrolysis in the small intestine and are thus largely undigested and unabsorbed (Gnoth et al. *J. Nutr.* 130, 3014 (2000); Engfer et al. *Am. J. Clin. Nutr.* 71,1589 (2000); Brand-Miller et al. *P. Nutr. Soc. Australia* 19, 44 (1995)). The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of *bifidobacterium* in the gut of breast-fed infants compared to a more diverse gut microbiota in formula-fed infants (Sela et al. *Trends Microbiol.* 18, 298 (2010); Bezirtzoglou et al *Anaerobe* 17, 478 (2011)). This is viewed as beneficial for the infant because strains of *bifidobacterium* species are believed to have a positive effect on gut health (Chichlowski et al. *J. Pediatr. Gastroenterol. Nutr.* 55, 123 (2012); Fukuda et al. *Nature* 469, 543 (2011); Peran et al. *J. Appl. Microbiol.* 103, 836 (2007)). However, it is not known if HMOs can stimulate the growth of bifidobacteria in the adult human intestine.

However, it is unclear how to effectively increase the abundance, particularly the relative abundance, of bifidobacteria, in particular a *Bifidobacterium* of the *B. adolescentis* phylogenetic group, especially *B. adolescentis* and/or *B. pseudocatenulatum*, in human microbiota. Genomic analyses of strains of *B. adolescentis* indicate that *B. adolescentis* has a nutrient acquisition strategy targeting plant-derived glycans, in particular starch and starch-like carbohydrates (Duranti et al. *Appl. Environ. Microbiol.* 80, 6080 (2014)). This fits with its increased abundance in older children and adolescence as the diet increasingly includes starches. However, many organisms in the gastro-intestinal tract target plant-derived glycans such as starch. Hence, feeding starches will not preferentially increase the abundance of *B. adolescentis* and/or *B. pseudocatenulatum* but rather will increase all the organisms able to metabolise starch. It may also be possible to administer *B. adolescentis* and/or *B. pseudocatenulatum* strains as probiotics. However, the long term viability of *B. adolescentis* and/or *B. pseudocatenulatum* strains in the gastro-intestinal tract is unclear. In in vitro tests, *B. adolescentis* generally shows no ability to grow in breast milk and utilise human milk oligosaccharides (Wittmann et al. *PLoS One* 8, e71338 (2013)), unlike *B. infantis*, *B. bifidum* and *B. breve* species. This is corroborated by the low relative absence of *B. adolescentis* in the infant intestinal tract.

SUMMARY OF THE INVENTION

There is a need, for means, preferably orally or enterally administered therapeutic and/or dietetic means, more preferably dietetic means, for effectively increasing the abundance, particularly the relative abundance, of a *Bifidobacterium* of the *B. adolescentis* phylogenetic group, especially *B. adolescentis* and/or *B. pseudocatenulatum*, in the microbiota of the gastro-intestinal tracts of humans, particularly non-infant humans.

The present invention relates to compositions and methods aimed to preferentially increase the abundance, particularly the relative abundance, of bifidobacteria, in particular a *Bifidobacterium* of the *B. adolescentis* phylogenetic group, especially *B. adolescentis* and/or *B. pseudocatenulatum*, in the microbiota in the gastro-intestinal tracts of humans.

A first aspect of this invention relates to an HMO, advantageously a neutral HMO, for use in increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of a human, preferably a non-infant human. Preferably, the HMO, advantageously a neutral HMO, is for use in increasing the abundance of a *Bifidobacterium* of the *B. adolescentis* phylogenetic group, especially *B. adolescentis* and/or *B. pseudocatenulatum*, in the gastro-intestinal tract of a human in order to treat or prevent in the human:
  an enteropathogenic infection,
  type 2 diabetes and/or obesity,
  impaired gut barrier function, and/or
  an inflammation related to a gastro-intestinal condition.

More preferably, the neutral HMO is a fucosylated neutral HMO, such as 2'-FL, 3-FL or DFL, or a mixture thereof, a non-fucosylated neutral HMO, such as LNnT or LNT, or a mixture thereof, or a mixture of a fucosylated and a non-fucosylated neutral HMO.

For increasing the abundance, particularly the relative abundance, of *B. adolescentis*, preferably a single HMO may be used, while for increasing the abundance, particularly the relative abundance, of *B. pseudocatenulatum* preferably two or more HMOs may be used.

A second aspect of the invention is a synthetic composition comprising an HMO, advantageously a neutral human milk oligosaccharide, for use in increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of a human, preferably to treat or prevent in the human:
  an enteropathogenic infection,
  type 2 diabetes and/or obesity,
  impaired gut barrier function, and/or
  an inflammation related to a gastro-intestinal condition.

The synthetic composition can be a nutritional or pharmaceutical composition.

Preferably, the neutral HMO is a fucosylated neutral human milk oligosaccharide, such as 2'-FL, 3-FL or DFL, a non-fucosylated neutral human milk oligosaccharide, such as LNnT or LNT, or a mixture of both.

A third aspect of this invention is a method for increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of a human, the method comprising orally or enterally administering to the human an effective amount of a human milk oligosaccharide, advantageously a neutral HMO.

A fourth aspect of this invention is a method for the prophylaxis or treatment of an enteropathogenic infection in a human, the method comprising orally or enterally administering, to the human, an amount of one or more human milk oligosaccharides, advantageously neutral HMOs, effective to preferentially increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human.

A fifth aspect of this invention is a method for the prophylaxis type 2 diabetes and/or obesity in a human or treatment of a human having type 2 diabetes and/or obesity, the method comprising orally or enterally administering, to said human, an amount of one or more human milk oligosaccharides, advantageously neutral HMOs, effective to preferentially increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human. Preferably, the amount is effective to preferentially increase the abundance of a *Bifidobacterium* of the *B. adolescentis* phylogenetic group, especially *B. adolescentis* and/or *B. pseudocatenulatum*. This may efficiently improve intestinal permeability and/or increase insulin sensitivity of said groups of humans.

A sixth aspect of this invention is a method for the prophylaxis or treatment of an inflammation related gastro-intestinal condition in a human, or treatment of a human having an inflammation related gastro-intestinal condition, the method comprising orally or enterally administering, to the human, an amount of one or more human milk oligosaccharides, advantageously neutral HMOs, effective to preferentially increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human. The gastro-intestinal condition may be intestinal bowel disease or irritable bowel syndrome. Preferably, the amount is effective to preferentially increase the abundance of a *Bifidobacterium* of the *B. adolescentis* phylogenetic group, especially *B. adolescentis* and/or *B. pseudocatenulatum*. This may efficiently improve an anti-inflammatory immune response in said human.

A seventh aspect of this invention is a method for the prophylaxis or treatment of impaired gut barrier function in a human, the method comprising orally or enterally administering, to the human, an amount of one or more human milk oligosaccharides, advantageously neutral HMOs, effective to preferentially increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human.

An eighth aspect of this invention is the use of an HMO, advantageously a neutral HMO, or a synthetic composition containing a HMO, advantageously a neutral HMO, in increasing the abundance of a *Bifidobacterium* of the *B. adolescentis* phylogenetic group, especially *B. adolescentis* and/or *B. pseudocatenulatum*, in the microbiota in the gastro-intestinal tract of a human, preferably in order to treat or prevent in said human an enteropathogenic infection,
type 2 diabetes and/or obesity,
impaired gut barrier function, and/or
an inflammation related to a gastro-intestinal condition.

Concerning any of the aspects disclosed herein, the human is preferably a non-infant human.

DETAILED DESCRIPTION OF THE INVENTION

It has now been surprisingly found by the present inventors that administration of human milk oligosaccharides to humans, preferably non-infant children and adults, preferentially increases the abundance of a *Bifidobacterium* of the *B. adolescentis* phylogenetic group, especially *B. adolescentis* and/or *B. pseudocatenulatum*, in the microbiota of their gastro-intestinal tract. Unlike in infants where administration of human milk oligosaccharides preferentially increases the abundance of *B. infantis, B. bifidum* and *B. breve* species, in non-infant children and adults, these species are not preferentially increased.

Thus it has been discovered that human milk oligosaccharides can, by oral or enteral ingestion, modulate the human, preferably non-infant, intestinal microbiota by preferentially promoting the growth of the species of the *B. adolescentis* phylogenetic group, especially *B. adolescentis* and/or *B. pseudocatenulatum*, and increase the abundance of this/these species in the human, preferably human non-infant, intestine. As an outcome, a more benign intestinal microbial community can be shaped and maintained, and by the increased abundance of a *Bifidobacterium* of the *B. adolescentis* phylogenetic group, especially *B. adolescentis* and/or *B. pseudocatenulatum*, pathogenic infections can be inhibited and intestinal and extra-intestinal diseases can be prevented or improved.

Herein, the following terms have the following meanings:

"*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. Appl. Environ. Microbiol. 79, 336 (2013), Bottacini et al. Microbial Cell Fact. 13:S4 (2014)). Preferably a *Bifidobacterium* of the *B. adolescentis* phylogenetic group is *Bifidobacterium adolescentis* and/or *Bifidobacterium pseudocatenulatum*.

"Non-infant human" or "non-infant" preferably means a human of 3 years of age and older. Accordingly, a non-infant human is a human of any age above 3 years old, e.g. it can be a child, a teenager, an adult or an elderly.

"Human milk oligosaccharide" or "HMO" preferably means a complex carbohydrate found in human breast milk (Urashima et al.: *Milk Oligosaccharides*. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition of the invention typically comprises one or more compounds, advantageously HMOs, that are capable of preferentially increasing the abundance of bifidobacteria, in particular a *Bifidobacterium* of the *B. adolescentis* phylogenetic group, especially *B. adolescentis* and/or *B. pseudocatenulatum*, in the microbiota of the gastro-intestinal tract. In some embodiments the synthetic composition may comprise one or more compounds or components other than HMOs that may have an effect on bifidobacteria of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

"Microbiota", "microflora" and "microbiome" preferably mean a community of living microorganisms that typically inhabits a bodily organ or part, particularly the gastro-intestinal organs of non-infant humans. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Enteral administration" preferably means any conventional form for delivery of a composition to a non-infant that causes the deposition of the composition in the gastrointestinal tract (including the stomach). Methods of enteral administration include feeding through a naso-gastric tube or jejunum tube, oral, sublingual and rectal.

"Oral administration" preferably means any conventional form for the delivery of a composition to a non-infant through the mouth. Accordingly, oral administration is a form of enteral administration.

"Effective amount" preferably means an amount of a composition that provides an HMO in a sufficient amount to render a desired treatment outcome in a non-infant. An effective amount can be administered in one or more doses to achieve the desired treatment outcome.

"Relative abundance of a *Bifidobacterium* of the *B. adolescentis* phylogenetic group" preferably means the abundance of a *Bifidobacterium* of the *B. adolescentis* phylogenetic group relative to other bifidobacteria in the microbiota of the gastro-intestinal tract of humans, preferably non-infants.

"Relative abundance of *B. adolescentis* and/or *B. pseudocatenulatum*" preferably means the abundance of *B. adolescentis* and/or *B. pseudocatenulatum* relative to other bifidobacteria in the microbiota of the gastro-intestinal tract of human, preferably non-infants.

"Relative growth of a *Bifidobacterium* of the *B. adolescentis* phylogenetic group" preferably means the growth of a *Bifidobacterium* of the *B. adolescentis* phylogenetic group relative to other bifidobacteria in the microbiota in the gastro-intestinal tract of humans, preferably non-infants.

"Relative growth of *B. adolescentis* and/or *B. pseudocatenulatum*" preferably means the growth of *B. adolescentis* and/or *B. pseudocatenulatum* relative to other bifidobacteria in the microbiota in the gastro-intestinal tract of humans, preferably non-infants.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

"Prophylaxis" means to prevent a development or re-occurrence a pathologic or undesirable condition in a human.

In accordance with this invention, it has been discovered that an HMO, preferably a neutral HMO, can promote the growth, particularly the relative growth, of a *Bifidobacterium* of the *B. adolescentis* phylogenetic group, especially *B. adolescentis* and/or *B. pseudocatenulatum*, in the microbiota in the gastro-intestinal tract of humans, preferably non-infants. For this reason, an HMO can be used for increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of humans, preferably non-infants. As a result, an HMO can be used for treating or preventing viral and/or bacterial infections (especially enteropathogenic infections), intestinal inflammatory diseases (especially IBS and IBD) and extra-intestinal diseases (especially obesity and type 2 diabetes) in humans, preferably non-infants.

Accordingly, the first aspect of the invention relates to an HMO, advantageously a neutral HMO, for increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of humans, preferably non-infants, and thereby treating and/or preventing viral and/or bacterial infections (especially enteropathogenic infections), intestinal inflammatory diseases (especially IBS and IBD) and extra-intestinal diseases (especially obesity and type 2 diabetes).

The second aspect of this invention relates to a synthetic composition comprising an HMO, advantageously a neutral HMO, for use in increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of a human, preferably a non-infant, and thereby treating and/or preventing viral and/or bacterial infections (especially enteropathogenic infections), intestinal inflammatory diseases (especially IBS and IBD) and extra-intestinal diseases (especially obesity and type 2 diabetes).

The neutral HMO of the first aspect and in the second aspect can preferably be one or more fucosylated HMOs, or one or more non-fucosylated HMOs. In one embodiment, the neutral HMO is a mixture of neutral HMOs, even preferably a mixture comprising or consisting of a fucosylated and a non-fucosylated neutral HMO. Particularly, the mixture contains or consists of a fucosylated neutral HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated neutral HMO selected from the list consisting of LNT, LNnT, LNH, LNnH, pLNH and pLNnH. In one preferred embodiment, the mixture contains or consists of a fucosylated neutral HMO selected from the list consisting of 2'-FL, 3-FL and DFL, and a non-fucosylated neutral HMO selected from the list consisting of LNT and LNnT. In some preferred embodiments the mixture comprises or consists of 2'-FL and LNnT.

The HMOs suitable for use in increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of non-infants can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2011/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

A synthetic composition of the invention can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antiviral agents, antibiotics, probiotics, analgesics, and anti-inflammatory agents. The proper dosage of these compositions for a non-infant human can be determined in a conventional manner, based upon factors such as immune status, body weight and age. In some cases, the dosage will be at a concentration similar to that found for the HMO, advantageously a neutral HMO, in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by conventional methods.

Pharmaceutical compositions of the invention can be used for treatment of a concerned disease in combination with other medicaments prescribed for said disease, e.g. in combination with an anti-diabetes medicine or antibiotic therapy.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition. Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for non-infants with inflamed GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for non-infants having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition may also include vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 μg/ml of lutein. Lycopene can be included in an amount from about 0.001 μg/ml to about 10 μg/ml, preferably about 0.0185 mg/ml to about 5 g/ml of lycopene. Beta-carotene can comprise from about 0.001 μg/ml to about 10 mg/ml, for example about 0.034 μg/ml to about 5 μg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be formulated as a soluble powder, a liquid concentrate, or a ready-to-use formulation. The composition can be fed to a human in need via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, it may be preferred that the total concentration of HMOs in the liquid, by weight of the liquid, is from about 0.0001% to about 2.0%, including from about 0.001% to about 1.5%, including from about 0.01% to about 1.0%.

When the nutritional product is a concentrated nutritional liquid, it may be preferred that the total concentration of HMOs in the liquid, by weight of the liquid, is from about 0.0002% to about 4.0%, including from about 0.002% to about 3.0%, including from about 0.02% to about 2.0%.

The synthetic composition comprising an HMO, preferably a neutral HMO or a mixture of neutral HMOs, such as a mixture of a fucosylated and a non-fucosylated neutral HMO disclosed above, can also be in a unit dosage form such as a capsule, tablet or sachet. For example, the synthetic composition can be in a tablet form comprising the HMOs, and one or more additional components to aid formulation and administration, such as diluents, excipients, antioxidants, lubricants, colorants, binders, disintegrants, and the like.

Examples of suitable diluents, excipients, lubricants, colorants, binders, and disintegrants include, but not limited to polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet form, can also include various nutrients including macronutrients.

According to this invention, a first target group of humans to whom an HMO or a composition comprising an HMO as described above can be administered includes healthy non-infant humans. Their ingestion of one or more HMOs, preferably a mixture of neutral HMOs, such as a mixture of a fucosylated and a non-fucosylated neutral HMO, will affect the composition of the intestinal microbiota by preferentially promoting the growth of a *Bifidobacterium* of the *B. adolescentis* phylogenetic group, especially *B. adolescentis* and/or *B. pseudocatenulatum*, which will increase its relative and absolute abundance in their gastro-intestinal tract.

A second target group of this invention includes non-infant humans with an enteropathogenic infection. Their ingestion of one or more HMOs, preferably a mixture of neutral HMOs, such as a mixture of a fucosylated and a non-fucosylated neutral HMO, will increase the intestinal abundance of a *Bifidobacterium* of the *B. adolescentis* phylogenetic group, especially *B. adolescentis* and/or *B. pseudocatenulatum*, and as a result, induce a favourable immune response against the enteropathogenic microorganism, inhibiting or treating infection.

A third target group for this invention includes obese non-infant humans, and/or lean or obese non-infant humans diagnosed with type 2 diabetes. Their ingestion of one or more HMOs, preferably a mixture of neutral HMOs, such as a mixture of a fucosylated and a non-fucosylated neutral HMO, increases the intestinal abundance of a *Bifidobacterium* of the *B. adolescentis* phylogenetic group, especially *B. adolescentis* and/or *B. pseudocatenulatum*, and as a result, improves intestinal permeability and/or increases insulin sensitivity, hence reducing the pathological conditions of type 2 diabetes and/or obesity.

A fourth target group for this invention includes non-infant humans diagnosed with intestinal diseases such as IBD and IBS. Their ingestion of one or more HMOs, preferably a mixture of neutral HMOs, such as a mixture of a fucosylated and a non-fucosylated neutral HMO, increases the intestinal abundance of a *Bifidobacterium* of the *B. adolescentis* phylogenetic group, especially *B. adolescentis* and/or *B. pseudocatenulatum*, and as a result, contributes to immunomodulation by inducing an anti-inflammatory immune response, hence improving symptoms.

Accordingly, the third aspect of this invention provides a method for increasing the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of a human, preferably a non-infant, the method comprising enterally, preferably orally, administering to the human:

an effective amount of one or more HMOs, or
a synthetic composition comprising an effective amount of one or more HMOs.

The fourth aspect of this invention relates to a method for the prophylaxis or treatment of an enteropathogenic infection in a human, preferably a non-infant human, the method comprising enterally, preferably orally, administering to the human:

an amount of one or more HMOs, or
a synthetic composition comprising an amount one or more HMOs, effective to increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human.

The fifth aspect of this invention provides a method for the prophylaxis or treatment of obesity and/or type 2 diabetes in a human, preferably a non-infant human, the method comprising enterally, preferably orally, administering to the human:

an amount of one or more HMOs, or
a synthetic composition comprising an amount of one or more HMOs, effective to increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human. This can efficiently improve the intestinal permeability and/or increase insulin sensitivity, and thereby beneficially contribute to the prevention of developing an obese state and/or type 2 diabetes in said human.

The sixth aspect of this invention provides a method for the prophylaxis or treatment of an inflammation related gastro-intestinal condition in a human, preferably a non-infant human, the method comprising enterally, preferably orally, administering to the human:

an amount of one or more HMOs, or
a synthetic composition comprising an amount of one or more HMOs, effective to increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human. According to the invention, this will induce an anti-inflammatory immune response in said human and thereby beneficially contribute to his/her condition. The gastro-intestinal condition is preferably intestinal bowel disease or irritable bowel syndrome.

The seventh aspect of this invention provides a method for the prophylaxis or treatment of impaired gut barrier function in a human, preferably a non-infant human, the method comprising enterally, preferably orally, administering to the human:
- an amount of one or more HMOs, or
- a synthetic composition comprising an amount of one or more HMOs, effective to increase the abundance, particularly the relative abundance, of a *Bifidobacterium* of the *B. adolescentis* phylogenetic group, especially *B. adolescentis* and/or *B. pseudocatenulatum*, in the microbiota in the gastro-intestinal tract of the human.

In the third to seventh aspects of therapeutic and prophylactic treatment of the invention, the HMO is advantageously a neutral HMO. The one or more neutral HMO can preferably be one or more fucosylated HMOs or one or more non-fucosylated HMOs. In one embodiment, the neutral HMO is a mixture of neutral HMOs, more preferably a mixture comprising or consisting of a fucosylated and a non-fucosylated neutral HMO. Particularly, the mixture contains or consists of a fucosylated neutral HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated neutral HMO selected from the list consisting of LNT, LNnT, LNH, LNnH, pLNH and pLNnH. Especially, the mixture contains or consists of a fucosylated neutral HMO selected from the list consisting of 2'-FL, 3-FL and DFL, and a non-fucosylated neutral HMO selected from the list consisting of LNT and LNnT, advantageously the mixture comprises or consists of 2'-FL and LNnT.

For increasing the abundance of a *Bifidobacterium* of the *B. adolescentis* phylogenetic group, especially *B. adolescentis* and/or *B. pseudocatenulatum*, in the gastro-intestinal tract of a human, preferably a non-infant human, the amount of HMO(s) required to be administered, i.e. an efficient amount, may vary depending upon factors such as the risk and severity of the obesity, type 2 diabetes, the inflammatory gastrointestinal condition or the enteropathogenic infection, age of the human, form of the composition, and other medications being administered. However, the required amount can be readily set by a medical practitioner. Typically, the amount of HMO/HMOs is in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, body weight and/or condition, the severity of the of type 2 diabetes, the inflammatory gastrointestinal condition or the enteropathogenic infection, being treated or prevented, other ailments and/or diseases, the incidence and/or severity of side effects and the manner of administration. Appropriate dose ranges may be determined by standard methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

In a yet further aspect, this invention relates to use of:
- an HMO, advantageously a neutral HMO, or
- a synthetic composition containing an HMO, advantageously a neutral HMO, in increasing the abundance of a *Bifidobacterium* of the *B. adolescentis* phylogenetic group, especially *B. adolescentis* and/or *B. pseudocatenulatum*, in the gastro-intestinal tract of a human, preferably a non-infant human, preferably in order to treat or prevent in the human:
- an enteropathogenic infection,
- type 2 diabetes and/or obesity,
- impaired gut barrier function, and/or
- an inflammation related to gastro-intestinal condition.

All embodiments of compositions and methods described above can also be used in this aspect of the invention.

Whilst the invention has been described with reference to a preferred embodiment, the aspects of the invention described above include multiple embodiments and therefore the scope of the invention is not limited to a preferred embodiment only.

EXAMPLES

The working example described herein are for illustration purposes only and should not be considered as limiting.

Example 1

A total of 100 male and female healthy adults are recruited to participate in the study. After a screening visit and run-in period of 1-2 weeks, the participants are selected and randomized into ten groups, each of 10 subjects. One group is administered a placebo product containing 2 grams of glucose. The remaining 9 groups are administered treatment product containing a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture of 2'-FL and LNnT, h) 10 g of a 2:1 mixture of 2'-FL and LNnT, and i) 5 g of a 2:1 mixture of 2'-FL and LNnT for 2 weeks (the amounts correspond to a daily dose). The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 2 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.
Additional, Gastrointestinal Symptom Rating Scale (GSRS) information.

This questionnaire includes 15 items covering five dimensions (abdominal pain, indigestion, reflux, diarrhea, constipation) and uses a seven-graded Likert scale.

At the end of the study, each participant has an exit visit with the medical team. Faecal samples and blood samples are collected.

Blood samples are analysed simultaneously in a multiplexing format on an electrochemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. *Nucleic Acids Res.* 41, e1 (2013)) with Illumina adapters attached. These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH is used for bioinformatical analysis of the sequence data.

To assess the *Bifidobacterium* community, ITS profiling of DNA samples is performed according to Milani et al. *FEMS Microbiol. Ecol.* 90, 493 (2014). Table 1 below shows the percentage increase of a *Bifidobacterium* species with high sequence similarity to *B. adolescentis* compared to that of other *Bifidobacterium* species identified in human faeces after consumption of HMOs as determined from faecal analyses. Additionally, the result from the profiling of the *Bifidobacterium* community shows that mainly the abundance of *B. adolescentis* increases when consuming a single HMO, whereas mainly the abundance of *B. pseudocatenulatum* increases when consuming a mix of two HMOs. Both *B. adolescentis* and *B. pseudocatenulatum* are members of the *B. adolescentis* phylogenetic group. It can be seen that oral ingestion of the HMOs clearly increases the abundance of *B. adolescentis* and/or *B. pseudocatenulatum* in the microbiota of healthy adults, as well as their relative abundance compared to the totality of other *Bifidobacterium* species.

TABLE 1

|  | *B. adolescentis* phylogenetic group | totality of *B. longum* + *B. bifidum* + *B. animalis lactis* + *B. angulatum* |
|---|---|---|
| a) 20 g 2'-FL | 120 | 15 |
| b) 10 g 2'-FL | 325 | 20 |
| c) 5 g 2'-FL | 50 | 0 |
| d) 20 g LNnT | 185 | 105 |
| e) 10 g LNnT | 195 | 130 |
| f) 5 g LNnT | 90 | 50 |
| g) 20 g mix | 320 | 265 |
| h) 10 g mix | 190 | 165 |
| i) 5 g mix | 25 | 20 |
| Placebo | 15 | −5 |

Example 2

Thirty 12 weeks old Male C57bl6/J mice are individually housed to avoid contamination between mice. Prior to the experiment, the mice are randomly assigned to three groups, ten mice in each group. The mice are fed three different experimental diets for 14 weeks. Group one is fed a standard diet (control) (Altromin; no. 1324); group two is fed a high-fat diet containing 60% fat (Research diet; no. D12492); Group three is fed a mix of HF-diet containing 60% fat (Research diet; no. D12492) and 5% of HMO (2'-FL and LNnT, mass ratio 2:1). Fresh water is administered daily and all mice have free access to drinking water.

Fresh faecal samples are collected at day −5, 0, 14, 28, 56, 84, 98. Samples are immediately frozen and stored at −80° C. until further analysis.

Oral glucose tolerance tests are performed after 13 weeks of treatment in mice that are fasted for 6 h. Glucose is orally administered (3 g/kg body weight, 660 g/l glucose solution) and blood glucose determined through a glucose meter using 3.5 µl of blood collected from the tip of the tail vein before and at administration of glucose load (−30 and 0 min) and after glucose load (15, 30, 60, 90 and 120 min). To assess plasma insulin concentration, 20 µl of blood is sampled 30 min before and 15 min following the glucose load.

Mice are euthanized by cervical dislocation after a 5 h period of fasting. Caecum (full and empty) and adipose tissues (epididymal, subcutaneous and visceral) are precisely dissected, weighed, immersed in liquid nitrogen and stored at −80° C., for further analysis.

Plasma LPS, cytokines and gut hormones are determined as follows. Plasma LPS concentration is measured using a kit based upon a Limulus amoebocyte extract (LAL kit endpoint-QCL1000). Samples are diluted 1/40 to 1/100 and heated for 20 cycles of 10 min at 68° C. and 10 min at 4° C. An internal control for LPS recovery is included in the calculation. Plasma cytokines (interleukin (IL) 1α, IL1b, tumour necrosis factor (TNF) α, IL6, monocyte chemoattractant protein (MCP)-1, macrophage inflammatory protein (MIP)-1α, IL10, interferon (INF) c, IL15, IL18) and gut hormones (GLP-1 (active), GIP (total), amylin (active), pancreatic polypeptide) are respectively determined in duplicate by using a Bio-Plex Multiplex kit, or a mouse gut hormones panel (LincoPlex), and measured by using Luminex technology, an EIA kit (GLP-2 EIA kit) is used to quantify GLP-2.

To determine the abundance of *B. adolescentis* and/or *B. pseudocatenulatum*, DNA is extracted from faecal samples and intestinal contents using QIAamp DNA Stool Mini Kit, and DNA concentration is measured using NanoDrop. The quantification of *B. adolescentis* and/or *B. pseudocatenulatum* is determined using quantitative PCR in a total reaction volume of 11 µl in 384-well microtiter plates using a LightCycler 480 II (Roche Applied Science). Each reaction will contain 1×SYBR green mix (Roche Applied Science), 0.2 pmol/µl of *B. adolescentis* and/or *B. pseudocatenulatum* specific primer (BiADO-1 ctc cag ttg gat gca tgt c/BiADO-2 cga agg ctt gct ccc agt) and total bacteria primer (HDA1 act cct acg gga ggc agc agt/HDA2 gta tta ccg cgg ctg ctg gca c), and 2 µl template DNA (1 ng/µl). Reaction conditions are: 95° C. for 5 min, 40 cycles of 95° C. for 10 sec, 60° C. for 15 sec, and 72° C. for 45 sec, followed by melting curve generation (95° C. for 5 sec, 65° C. for 1 min and increasing the temperature to 98° C. with a rate of 0.11° C./sec with continuous fluorescence detection). Data is initially analysed in the LightCycler® 480 software. Noise band and threshold are set automatically using the LightCycler® 480 software. Cq-values are used for data analysis. The relative abundances of *B. adolescentis* and/or *B. pseudocatenulatum* normalized to the total number of 16S rRNA genes (total bacteria primer) are calculated.

To assess the microbiota profile, DNA is extracted from faecal samples and intestinal contents using QIAamp DNA Stool Mini Kit. The DNA concentration of extracts is measured using NanoDrop. The bacterial composition is determined by sequencing, as described in Example 1.

The results show that oral ingestion of HMOs modulate the intestinal microbiota, and increase the abundance of bifidobacteria, in particular a *bifidobacterium* of the *B. adolescentis* phylogenetic group, especially *B. adolescentis* and/or *B. pseudocatenulatum*. Additionally, the results show that bifidobacteria of the *B. adolescentis* phylogenetic group, especially *B. adolescentis* and/or *B. pseudocatenulatum*, negatively correlate with glucose intolerance, fasted insulinaemia, inflammatory markers, adipose tissue and body weight gain. Collectively, HMOs are able to increase bifidobacteria of the *B. adolescentis* phylogenetic group, especially *B. adolescentis* and/or *B. pseudocatenulatum*, and by this, reduce endotoxaemia and improve glucose tolerance and insulin secretion, as well as reducing inflammation development in HF-diet-fed mice.

The invention claimed is:

1. A method for increasing the abundance of a *Bifidobacterium* of the *B. adolescentis* phylogenetic group in the microbiota in the gastro-intestinal tract of a non-infant human, the method comprising enterally administering to the a non-infant human a synthetic composition comprising an effective amount of one or more human milk oligosaccharide components,
    wherein the one or more human milk oligosaccharide components comprise a human milk oligosaccharide selected from the group consisting of 2'-fucosyllactose (2'-FL), 3-fucosyllactose (3-FL), difucosyllactose (DFL), lacto-N-tetraose (LNT) and lacto-N-neotetraose (LNnT), or a mixture thereof, and
    wherein the synthetic composition is not identical to a naturally occurring composition.

2. The method of claim 1, wherein the synthetic composition further comprises one or more human milk oligosaccharide components selected from the group consisting of lacto-N-neohexaose (LNnH), para-lacto-N-neohexaose (pLNnH), para-lacto-N-hexaose (pLNH) and lacto-N-hexaose (LNH), lacto-N-fucopentaose I (LNFP-I), lacto-N-difucohexaose I (LNDFH-I), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-1), fucosyl-para-lacto-N-neohexaose II (FpLNnH II) and fucosyl-lacto-N-neohexaose (FLNnH), 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-Nneohexaose II (SLNH-II) and disialyl-lacto-N-tetraose (DSLNT); or a mixture thereof.

3. The method of claim 1, wherein the synthetic composition further comprises one or more human milk oligosaccharide components selected from the group consisting of lacto-N-fucopentaose I (LNFP-I), lacto-N-fucopentaose II (LNFP-II), lacto-N-fucopentaose III (LNFP-III) and lacto-N-fucopentaose V (LNFP-V), or a mixture thereof.

4. The method of claim 1, wherein synthetic composition further comprises one or more human milk oligosaccharide components selected from the group consisting of 3'-sialyllactose (3'-SL), or a mixture thereof.

5. The method of claim 1, wherein the non-infant human is an adult or an elderly person.

6. The method of claim 1, wherein the non-infant human suffers from an enteropathogenic infection.

7. The method of claim 1, wherein the synthetic composition is a pharmaceutical composition.

8. The method of claim 1, wherein the synthetic composition is a nutritional composition.

9. The method of claim 1, wherein the abundance of a *Bifidobacterium* of the *B. adolescentis* phylogenetic group is a relative abundance.

10. The method of claim 9, wherein the *Bifidobacterium* of the *B. adolescentis* phylogenetic group is *B. adolescentis* and/or *B. pseudocatenulatum*.

11. The method of claim 1, wherein the one or more human milk oligosaccharide components comprise a mixture of 2'-FL and LNnT.

12. The method of claim 1, wherein the one or more human milk oligosaccharide components comprise LNT, LNnT, or a mixture of LNT and LNnT.

13. The method of claim 1, wherein the one or more human milk oligosaccharide components comprises 2'-FL, DFL, or a mixture of 2'-FL and DFL.

14. The method of claim 1, wherein the one or more human milk oligosaccharide components comprise 2'-FL, 3-FL, DFL, or a mixture of any of the foregoing.

15. The method of claim 1, wherein the one or more human milk oligosaccharide components comprise 2'-FL, DFL, LNnT, or a mixture of any of the foregoing.

16. The method of claim 1, wherein the one or more human milk oligosaccharide components comprise a mixture of (a) at least one human milk oligosaccharide selected from the group consisting of 2'-FL, 3-FL and DFL, and (b) at least one human milk oligosaccharide selected from the group consisting of LNT and LNnT.

* * * * *